(12) United States Patent
Wilkens et al.

(10) Patent No.: US 8,183,541 B2
(45) Date of Patent: May 22, 2012

(54) INVERSE TREATMENT PLANNING METHOD

(75) Inventors: Jan Wilkens, Munich (DE); Uwe Oelfke, Monchzell (DE)

(73) Assignee: Deutsches Krebsforschungszentrum des Oeffentlichen Rechts, Heidelberg (DE)

( * ) Notice: Subject to any disclaimer, the term of this patent is extended or adjusted under 35 U.S.C. 154(b) by 806 days.

(21) Appl. No.: 12/223,712

(22) PCT Filed: Feb. 2, 2007

(86) PCT No.: PCT/EP2007/051036
§ 371 (c)(1),
(2), (4) Date: Sep. 30, 2008

(87) PCT Pub. No.: WO2007/090798
PCT Pub. Date: Aug. 16, 2007

(65) Prior Publication Data
US 2009/0060130 A1 Mar. 5, 2009

(30) Foreign Application Priority Data
Feb. 9, 2006 (EP) .................................. 06101441

(51) Int. Cl.
*G21K 5/04* (2006.01)

(52) U.S. Cl. ................. 250/492.1; 250/492.3; 600/1

(58) Field of Classification Search .............. 600/1, 2; 607/1; 250/491.1, 492.1, 492.3
See application file for complete search history.

(56) References Cited

U.S. PATENT DOCUMENTS

2005/0167616 A1* 8/2005 Yanagisawa et al. ..... 250/492.22
2010/0320402 A1* 12/2010 Wu et al. .................... 250/492.1

OTHER PUBLICATIONS

Wilkens et al. "Optimization of radiobiological effects in intensity modulated proton therapy", American Association of Medical Physics 32(2), Jan. 2005 pp. 455-465.*
Nill et al., Zeitschrift fur medizinische Physik 14(1) (2004) 35-40.
Wilkens et al., Phys. Med. Biol. 49 (2004) 2811-2825.
Jan J. Wilkens, Med. Phys., vol. 31, No. 10, Oct. 2004, p. 2934.

(Continued)

*Primary Examiner* — David A Vanore
*Assistant Examiner* — Nicole Ippolito
(74) *Attorney, Agent, or Firm* — Birch, Stewart, Kolasch & Birch, LLP

(57) ABSTRACT

The invention relates to a radiation treatment apparatus and an inverse treatment planning method for intensity modulated particle therapy for the treatment of a target within a biological system using at least two fields, each field comprising a plurality of Bragg peaks, the at least two fields being planned to place a defined number of beam spots j from different directions with certain weights $w_j$ within the target. The inverse treatment planning method optimizes the weights $w_j$ of the beam spots for the at least two fields simultaneously in order to produce a prescribed biological effect within the target by minimizing an objective function based on biological effects $\epsilon$, the biological effects $\epsilon$ being treated in a linear-quadratic model, which describes the biological effects in the target by two parameters $\alpha$ and $\beta$, where $\epsilon = \alpha D + \beta D^2$, D denoting a dose, and wherein the two parameters $\alpha$ and $\beta$ for each voxel i of the target ($\alpha_i$ and $\beta_i$) are calculated as dose-averaged mean values of $\alpha_{i,j}$- and $\sqrt{\beta_{i,j}}$-components, which relate to all beam spots j contributing to a total dose $D_i$ in the voxel i.

9 Claims, 1 Drawing Sheet

OTHER PUBLICATIONS

Jan J. Wilkens, Dissertation, [Online] May 2004, University of Heidelberg, Germany, Heidelberg, [retrieved on May 30, 2006] p. 52-p. 59, p. 8-p. 14, p. 30, p. 87-p. 90, p. 10-p. 13, pp. 69, 84, 26, pp. 28, 90, p. 63-p. 86, pp. 47-51, figures 4.5, 2.3, 4.1, 3.9; table 5.3.

Schaffner et al., Med. Phys., vol. 27, No. 4, Apr. 2000, pp. 716-724.

Kraft G., Nuclear Instruments & Methods in Physics Research, Section—A—: Accelerators, Spectrometers, Detectors and Associated Equipment, Elsevier, Amsterdam, NL, vol. 454, No. 1, Nov. 1, 2000, pp. 1-10.

* cited by examiner

INVERSE TREATMENT PLANNING METHOD

FIELD OF THE INVENTION

The present invention relates to inverse treatment planning for radiotherapy with ion beams. The inverse treatment planning is applicable to the so-called intensity modulated particle therapy (IMPT), which refers to a treatment technique using several fields which in total produce a desired distribution of the biological effect in the anatomy of a radiation therapy patient.

BACKGROUND OF THE INVENTION

Besides surgery and chemotherapy, radiation therapy is one of the three main options for treating tumor patients. Over the last years, advances in research and technology led to significant improvements in all fields of radiotherapy. While the majority of irradiation is done by high energy photons, another promising approach is the treatment with ion beams. Due to the different depth dose characteristic of charged particles compared to X-rays, superior dosed distributions in the patient and, therefore, higher tumor control and less side effects can be anticipated for treatments with ion beams.

The treatment with proton and heavy ion beams enjoys a rising interest. The most sophisticated technique in proton therapy is intensity modulated proton therapy, which involves narrow beam spots that are delivered to the patient in a scanning pattern. The intensity of the beam spots is modulated individually, and their relative weights are determined by an optimization algorithm to obtain the best possible treatment plan. This process is called inverse treatment planning, since it solves the problem of automatically finding the best set of treatment parameters for a given (prescribed) dose distribution rather than the other way round, which was the conventional approach in treatment planning systems.

Today inverse planning for protons is based on fast and reliable algorithms for dose calculations (care for Nill, Bortfeld, Oelfke, "Inverse Planning of Intensity Modulated Proton Therapy", Zeitschrift für medizinische Physik 14(1) (2004) 35-40). However, the physical dose is apparently not the only parameter one should look at in treatment planning for protons and ions, as there is experimental evidence that the biological effect caused by charged particle beams does not depend on the physical dose alone, but also on the energy spectrum of the beam. In other words: the same physical dose delivered by protons or by ions with an atomic number $\geq 2$ of different energy does not lead to the same biological results (e.g. in terms of cell survival). Therefore, it is not sufficient to consider the physical dose alone. Instead, 3-dimensional variations of the relative biological effectiveness (RBE) have to be taken into account (care for Wilkens, Oelfke: "A phenomenological model for the relative biological effectiveness in therapeutic proton beams", Phys. Med. Biol. 49 (2004) 2811-2825). The RBE is defined as the ratio of the dose of a reference radiation and the respective charged particle dose required to yield the same biological effect (e.g. cell survival). This means, that in inverse planning for intensity modulated radiotherapy with ion beams using scanning beam delivery techniques, the biological effect (RBE*dose) has to be optimized rather than the physical dose distribution.

Some inverse planning methods known in the state of the art take the biological effect into account. However, these methods do not permit a simultaneous multifield optimization. Furthermore, they require long computing times for the iterative optimization of the treatment plan. Additionally, these prior art methods cannot account for the common case of mutually conflicting optimization goals (e.g. high and homogeneous effect in the target and sparing of organs at risk or healthy tissue).

SUMMARY OF THE INVENTION

Therefore, the present invention is based on the object of avoiding the disadvantages of the prior art and especially of presenting a fast method for simultaneous multifield optimization of the biological effect in intensity modulated radiotherapy with ion beams. In particular, the method should allow for complete inverse treatment planning, the optimization being based on constraints in biological effective dose for radiation targets and organs at risk.

These objects are achieved by an inverse treatment planning method for intensity modulated particle therapy for the treatment of a target within a biological system using at least two fields, each field comprising a plurality of Bragg peaks, the at least two fields being planned to place a defined number of beam spots (j) from different directions with certain weights $w_j$ within the target. This inverse treatment planning method optimizes the weights $w_j$ of the beam spots for the at least two fields simultaneously in order to produce a prescribed biological effect within the target by minimizing an objective function based on biological effects $\epsilon$, which are treated in a linear-quadratic model, which describes the biological effects in the target by two parameters $\alpha$ and $\beta$, where $\epsilon = \alpha D + \beta D^2$, D denoting a dose, and wherein the two parameters $\alpha$ and $\beta$ for each voxel i of the target ($\alpha_i$ and $\beta_i$) are calculated as dose-averaged mean values of $\alpha_{i,j}$- and $\sqrt{\beta_{i,j}}$-components, which relate to all beam spots j contributing to a total dose $D_i$ in the voxel i.

In this context intensity modulated particle therapy (IMPT) is used similar to the term intensity modulated radiotherapy (IMRT) for ion beams and is understood as an irradiation technique using several fields (beam ports), that each create an inhomogeneous distribution of the biological effect in the target. Every field consists of a high number of individual Bragg peaks (beam spots or scan positions), whose weights are optimized. In total the fields produce the desired distribution of the biological effect in the target.

The inverse treatment planning method according to the present invention is preferably applied for planning the treatment of a target with protons as the lightest ion species or for beams of ions with an atomic number, which is equal to or larger than 2, e.g. carbon ions. It can be used for treatment planning for all radiation types that show a spatially variable relative biological effectiveness (RBE). A target to be treated within a biological system is for example a tumor in the body of a patient.

Naturally the method according to the present invention also allows for inverse planning of the biological effect for single field charged particle beams (spread-out Bragg peaks). The innovative feature of this approach is that radiation targets and organs at risk can be considered simultaneously in the optimization process. Furthermore, the method accounts for different ratio-sensitivities of different tissues as characterized by different $\alpha$ and $\beta$ values.

With the method according to the present invention, the treatment of a target with a defined number of beam spots j from different directions with certain weights $w_j$ is planned. For the delivery of intensity-modulated charged particle beams, a spot or raster scanning device is commonly used. Therefore, for each beam spot not only the weight has to be optimized, but also the in-depth position of the Bragg peak for the beam spots which is directly correlated to the energy of the incident particles has to be defined. To sample the tumor volume with a scanning device many beam spots must be placed at different positions inside the target. The main differences between known scanning techniques are the positions and the number of beam spots used. Two of these methods are e.g. the distal edge tracking (DET) and the 3D-technique. The Bragg peak position of all beam spots used by the distal edge tracking technique is placed at the distal edge of the target only. To track the distal edge of the tumor, either an active energy variation or passive range shifter (material inserted into the beam to reduce the energy of the particles) can be used for every spot. For the lateral distribution of the beam spots a regular scanning grid is used (magnetic sweeping). For the 3D-technique the Bragg peaks of the beam spots are not only placed at the distal edge of the tumor, but also inside the tumor. The spot positions (Bragg peaks) used inside the tumor mainly depend on the scanning device. For the inverse treatment planning method according to the present invention, the number and directions of the needle beams of charged particles and the positions of the beam spots j to be placed by these needle beams within the target to be irradiated are part of the input data used in the optimization approach. The selection of the spot position can be done automatically by a planning tool. The weights $w_j$ of each of these beam spots, which define the number of charged particles delivered to the spots, are optimized by the planning method according to the invention.

One advantage of the present invention is that it allows for a multifield optimization. The biological effect is optimized simultaneously for the at least two fields The weights $w_j$ of the beam spots j of the at least two fields are optimized at the same time and not independent of one another in order to produce a prescribed biological effect in the target. The biological effect determines for instance the survival fraction $S(D)/S_0$ of cells of a certain dose D.

In inverse treatment planning methods according to the state of the art the optimization is usually done be minimizing an objective function based on doses, e.g. a quadratic objective function of the formula $$F_D(\vec{w}) = \sum_{i \in T} (D_i(\vec{w}) - D_T)^2$$

where the quadratic difference between the dose $D_i$ and the prescribed dose $D_T$ is summed up for all voxels i in the target T. Similar appropriate constraints are also formulated for organs at risk. The optimization is done by minimizing this dose-based objective function using iterative algorithms. The aim is to find a set of weights $\vec{w}$ so that the resulting dose matches the desired clinical objectives.

The planning method according to the present invention directly optimizes the biological effect by using an effect-based objective function instead of the dose-based objective function. Therefore, the dose D is substituted by the biological effect $\epsilon$. To obtain a homogeneous biological effect in the target, the dose is substituted by the biological effect from the known linear-quadratic model. The linear-quadratic model describes the biological effects by two response parameters $\alpha$ and $\beta$ and by the dose D with $\epsilon = \alpha D + \beta D^2$.

The prescribed biological effect $\epsilon_T$ is for example given by $\epsilon_T = \alpha_T^X D_T + \beta_T^X D_T^2$, where $\alpha_T^X$ and $\beta_T^X$ are the X-ray response parameters of the target and $D_T$ the prescribed photon dose. The ion response is calculated using $\alpha_i(\vec{w})$ and $\beta_i(\vec{w})$. As biological input for the optimization in the inverse treatment planning method according to the invention, the 3-dimensional distribution of $\alpha$ and $\beta$ in the target is required for every beam spot separately, i.e. $\alpha_{i,j}$ and $\beta_{i,j}$ matrices, where i denotes the voxel and j the beam spot. These matrices have to be computed only once before the optimization, which makes the whole procedure very fast. The values of $\alpha_{i,j}$ and $\beta_{i,j}$ depend on the tissue type at voxel i, on the depth the radiation has to penetrate before it reaches the voxel, on the lateral distance of the voxel from the central axis and on dosimetric properties (e.g. the initial energy) of spot j. For a given beam spot, these values already contain the total effect due to primary and all secondary particles which are generated in nuclear interaction and fragmentation processes. The full $\alpha_{i,j}$ and $\beta_{i,j}$ matrices are relatively large, but they can be reduced to relatively few values by approximations. The optimization itself is completely independent of how these matrixes were calculated, which makes the method according to the present invention extremely flexible regarding the biological input data. In principle, one can use any radiobiological model (e.g. the local effect model—LEM) or even directly measured data for $\alpha$ and $\beta$ as a function of depth in the single Bragg peak.

In the inverse treatment planning method according to the present invention the two parameters $\alpha_i$ and $\sqrt{\beta_i}$ for each voxel i of the target are calculated as dose-averaged mean values of $\alpha_{i,j}$- and $\sqrt{\beta_{i,j}}$-components which relate to all N beam spots j contributing to a total dose $D_i$ in the voxel i. With a set of N beam spots irradiating a target and $D_{i,j}$ denoting the dose contribution to voxel i per unit fluence of beam spot j, the total dose $D_i$ in the voxel i is given by $$D_i = \sum_{j=1}^{N} w_j D_{i,j}$$

where $w_j$ denotes the relative fluence weight of beam spot j. By including all N beam spots j of all of the at least two fields into this calculation of $\alpha_i$, $\beta_i$ and $D_i$, a simultaneous multifield optimization is possible by minimizing the effect-based objective function.

The effect-based objective function can include constraints like minimum and maximum effect levels for targets or maximum effects for organs at risk. Therefore, the inverse treatment planning method according to the present invention can include various optimization aims.

According to a preferred embodiment of the present invention an objective function is minimized, which is based on the form $$F_\varepsilon(\vec{w}) = \sum_{i \in T} (\varepsilon_i(\vec{w}) - \varepsilon_T)^2$$

with $\epsilon_i$ denoting the biological effect in the voxel i of the target, $\vec{w}$ the weights of the beam spots and $\epsilon_T$ the prescribed biological effect of a reference radiation. Preferably an objective function is minimized which is based on the form $$F_\varepsilon(\vec{w}) = \sum_{i \in T} (\alpha_i(\vec{w}) D_i(\vec{w}) + \beta_i(\vec{w}) D_i^2(\vec{w}) - \varepsilon_T)^2$$

with $D_i$ denoting the total dose of the at least two fields in voxel i and $\alpha_i$ and $\beta_i$ the $\alpha$ and $\beta$-values at voxel i, wherein $$D_i = \sum_{j=1}^{N} w_j D_{i,j}$$

with $D_{i,j}$ denoting a dose contribution of beam spot j at voxel i for a unit fluence, N beam spots contributing to the dose $D_i$ at voxel i and $w_j$ denoting a weighting factor of beam spot j and wherein the prescribed biological effect ($\epsilon_T$) is given by $$\epsilon_T = \alpha_T^x D_T + \beta_T^x D_T^2$$

with $\alpha_T^x$ and $\beta_T^x$ being X-ray response parameters of the target and $D_T$ denoting a prescribed photon dose. Minimizing this objective function will lead to a prescribed biological effect and, therefore, to the required distribution of the product of relative biological effectiveness and dose, e.g. a respective homogeneous distribution in the radiation target.

Furthermore, in the inverse treatment planning method according to the present invention an objective function can be minimized, which also includes constraints relating to minimum and maximum biological effect levels for the target and maximum effect levels for organs at risk within the biological system.

According to a preferred embodiment of the present invention, the two parameters $\alpha$ and $\beta$ for each voxel i of the target ($\alpha_i$ and $\beta_i$) are calculated as dose-averaged mean values of the form $$\alpha_i = \frac{1}{D_i} \sum_{j=1}^{N} w_j D_{i,j} \alpha_{i,j} \text{ and}$$

$$\sqrt{\beta_i} = \frac{1}{D_i} \sum_{j=1}^{N} w_j D_{i,j} \sqrt{\beta_{i,j}}$$

for $$D_i > 0, D_i = \sum_{j}^{N} w_j D_{i,j},$$

with N beam spots contributing to the total dose $D_i$ in voxel i. $D_{i,j}$ is the dose contribution for unit fluence from beam spot j and $w_j$ is a weighting factor.

Preferably the $\alpha_{i,j}$- and $\sqrt{\beta_{i,j}}$-components are derived from a radiobiological model or from directly measured data for $\alpha$ and $\beta$ as a function of depth in a single Bragg peak.

The inverse treatment planning method according to the present invention provides a great flexibility for the biological input. If desired, very complex algorithms can be used to fill the $\alpha_{i,j}$- and $\beta_{i,j}$-matrices, which does not affect the speed for the optimization itself.

According to one embodiment of the present invention a constant value $\beta_{i,j} = \beta_i$ is set, which depends only on a tissue type at voxel i. This approximation reduces the $\beta_{i,j}$-matrix to relatively few values and, therefore, has a shortening effect on computation times for the inverse treatment planning. In therapeutic situations with high linear energy transfer radiations, it is anticipated that $\alpha$ is more important than $\beta$, i.e. that the $\alpha/\beta$-ratio is relatively high for these radiations, and the RBE is mostly determined by variations in the $\alpha$ parameter. Variations in $\beta$ are less important, especially for therapeutic doses per fraction well below 5 Gy, which justifies the introduction of a coarse approximation for $\beta$. To keep the $\beta_{i,j}$-matrix as simple as possible, a constant $\beta$ is assumed and it is set, e.g. to the value of $\beta^X$ for the reference radiation, i.e. $\beta_{i,j} = \beta_i = \beta_i^X$. This depends only on the tissue type at voxel i.

According to one embodiment of the present invention the $\alpha_{i,j}$-components are assumed to be laterally constant and are extracted from a single curve as a function of residual range, independent of an initial beam energy. The calculation of $\alpha_{i,j}$ for given j can be done in close analogy to dose calculation algorithms by factorization into a central axis term $\alpha_{cax}(z)$ (corresponding to the depth dose curve at depth z) and a depth-dependent off-axis term $\alpha_{lat}(r, z)$, where r is the distance of voxel i from the central axis of spot j. For simplification, the off-axis behaviour is ignored by setting $\alpha_{lat}(r, z) = 1$, i.e. a laterally constant $\alpha$ is assumed. This means that lateral variations in the local particle spectra are not accounted for, e.g. for the slight decrease of the mean energy of the primary particles with increasing r and the greater importance of scattered secondaries far from the central axis. These effects are, however, relatively small, and they are not expected to have a strong impact on the lateral RBE distribution, which is mainly given by an increase with r due to the decreasing dose. Furthermore, it turned out that $\alpha_{cax}$ as a function of residual range is not very sensitive to changes in the initial beam energy.

The present invention further refers to the use of the inverse treatment planning method according to the invention for planning the treatment of a tumor with ion beams, preferably with beams of ions with an atomic number $\geq 2$, most preferably with carbon ion beams.

The present invention further refers to a radiation treatment apparatus for delivering a radiation treatment to a target within a biological system comprising means for generating at least two fields, each field comprising a plurality of Bragg peaks, the at least two fields being provided to place a defined number of beam spots j from different directions with certain weights $w_j$ within the target. The radiation treatment apparatus further comprises means for inverse treatment planning, being provided for optimizing the weights $w_j$ of the beam spots for the at least two fields simultaneously before the radiation treatment in order to produce a prescribed biological effect within the target by minimizing an objective function based on biological effects $\epsilon$, the biological effects $\epsilon$ being treated in a linear-quadratic model, which describes the biological effects in the target by two parameters $\alpha$ and $\beta$, where $\epsilon = \alpha D + \beta D^2$, D denoting a dose, and wherein the two parameters $\alpha$ and $\beta$ for each voxel i of the target ($\alpha_i$ and $\beta_i$) are calculated as dose-averaged mean values of $\alpha_{i,j}$- and $\sqrt{\beta_{i,j}}$-components, which relate to all beam spots j contributing to a total dose $D_i$ in the voxel i. Preferably the radiation treatment apparatus of the present invention comprises means to carry out all of the steps of the inverse treatment planning method according to the present invention as described above.

EXAMPLE

To demonstrate the potential of the multifield optimization of the inverse treatment planning method according to the present invention, a 1-dimensional example of two opposing fields that are optimized simultaneously, is presented. This is compared to a single-field optimization, where both fields are optimized separately, before they are added up in a final calculation step. The target of 38 mm length was assumed to be located in the centre of a 254 mm thick phantom. The aim of the optimization was to deliver 3 GyE in the target and to spare the tissue outside of the target (defined as an organ at risk) as much as possible. A chordoma data set of $\alpha_{i,j}$ and $\beta_{i,j}$ was used throughout the phantom. The same parameters can also be employed to describe the limiting late reactions in human brain tissue. For single-field optimization, each field was optimized to yield 1.89 GyE in the target, which added up to a total of 3 GyE.

Figure 1:
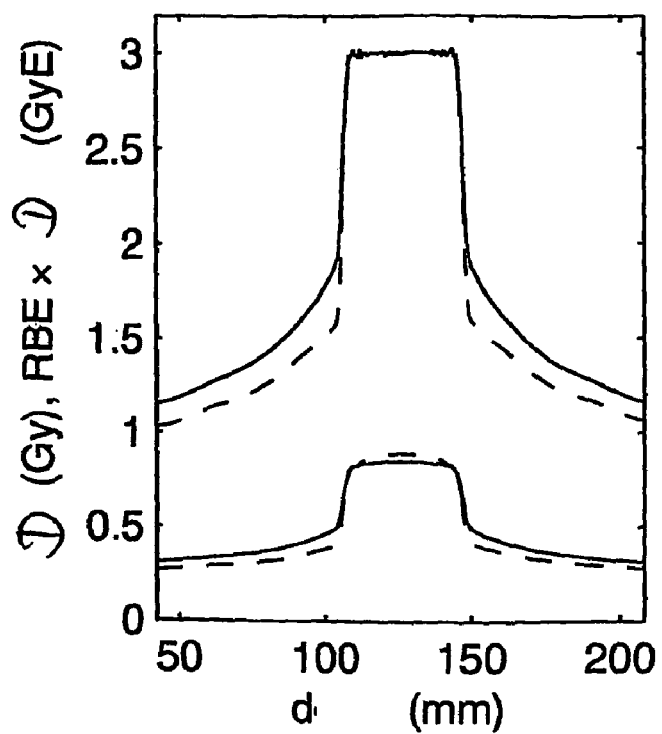
FIG. 1 illustrates results for the total distributions for dose and RBE × dose in an exemplary embodiment.

Results for the total distributions for dose and RBE*dose are shown in FIG. 1. The upper line pair shows RBE*dose depending upon the depth d and the lower line pair shows the physical dose D depending upon the depth d for the 2-field-plan using two symmetric, opposing beam ports with carbon ions in water (biological target: chordoma cells). The results are given for the single-field optimization (continuous line), where each field was optimized separately, and for simultaneous multifield optimization according to the method of the present invention (dashed line). While both optimization methods yield a homogeneous biological effect of the same level in the target, an increased sparing of normal tissue for the multifield optimization according to the invention is clearly visible.

Figure 2:
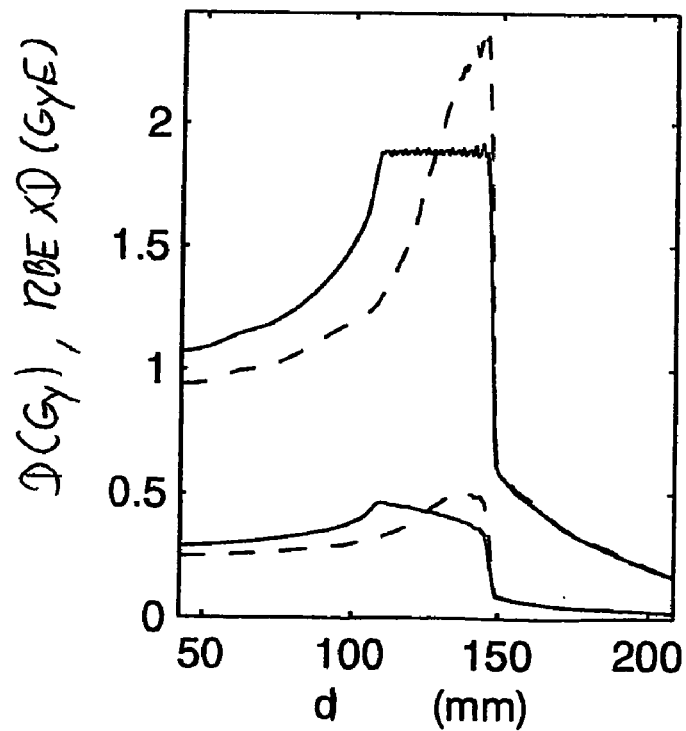
FIG. 2 illustrates contributions for the left lateral field only for a case where the right lateral field is symmetric to the left field, in an exemplary embodiment.

FIG. 2 gives the contributions for the left lateral field only (right lateral field is symmetric to the left one). The upper lines show the RBE*dose and the lower lines the physical dose D contributed from the field incident from the left. This clearly illustrates the difference between single-field (continuous line) and multifield (dashed line) optimization. For multifield optimization, the biological effect for one beam only is not homogeneous in the target. Instead, higher doses are delivered in the distal part of the target. These inhomogeneous subfields resemble a "distal edge tracking" like solution. Since beam spots in the distal part of the target have the best "dose-to-target/dose-to-normal-tissue" ratio, the normal tissue can be spared better using this type of inhomogeneous subfields in combination with the multifield optimization according to the present invention.

Therefore, it was found that the treatment plans resulting from the method according to the present invention could be enhanced considerably e.g. by improved sparing of the normal tissue and organs at risk. The high number of degrees of freedom in treatment planning for ions can be exploited better using intensity modulated particle therapy and multifield optimization in the method of the invention. Furthermore, this method can provide the advantages of a multifield plan with a moderate number of beam spots for time-efficient optimization.

The invention claimed is:

1. An inverse treatment planning method for intensity modulated particle therapy for the treatment of a target within a biological system using at least two fields, each field comprising a plurality of Bragg peaks, the at least two fields being planned to place a defined number of beam spots j from different directions with certain weights $w_j$ within the target, wherein the inverse treatment planning method optimizes the weights $w_j$ of the beam spots for the at least two fields simultaneously in order to produce a prescribed biological effect within the target by minimizing an objective function based on biological effects $\epsilon$, the biological effects $\epsilon$ being treated in a linear-quadratic model which describes the biological effects in the target by two parameters $\alpha$ and $\beta$, where $\epsilon=\alpha D+$ $\beta D^2$, D denoting a dose, and wherein the two parameters $\alpha$ and $\beta$ for each voxel i of the target $\alpha_i$ and $\beta_i$ are calculated as dose-averaged mean values of $\alpha_{i,j}$- and $\sqrt{\beta_{i,j}}$-components, which relate to all beam spots j contributing to a total dose $D_i$ in the voxel i, wherein the two parameters $\alpha$ and $\beta$ for each voxel i of the target ($\alpha_i$ and $\beta_i$) are calculated as dose-averaged mean values of the form $$\alpha_i = \frac{1}{D_i}\sum_{j=1}^{N} w_j D_{i,j} \alpha_{i,j} \text{ and}$$

$$\sqrt{\beta_i} = \frac{1}{D_i}\sum_{j=1}^{N} w_j D_{i,j} \sqrt{\beta_{i,j}}$$

for $D_i > 0$, $$D_i = \sum_{j=1}^{N} w_j D_{i,j}$$

with N beam spots contributing to the total dose $D_j$ in voxel i.

2. The inverse treatment planning method according to claim 1, wherein an objective function is minimized, which is based on the formula $$F_\epsilon(\vec{w}) = \sum_{i \in T} (\epsilon_i(\vec{w}) - \epsilon_T)^2$$

with $\epsilon_i$ denoting the biological effect in the voxel i of the target, $\vec{w}$ the weights of the beam spots and $\epsilon_T$ the prescribed biological effect of a reference radiation.

3. The inverse treatment planning method according to claim 1, wherein an objective function is minimized, which is based on the formula $$F_\epsilon(\vec{w}) = \sum_{i \in T} (\alpha_i(\vec{w}) D_i(\vec{w}) + \beta_i(\vec{w}) D_i^2(\vec{w}) - \epsilon_T)^2$$

with $D_i$ denoting the total dose of the at least two fields in voxel i and $\alpha_i$ and $\beta_i$ the $\alpha$- and $\beta$-values at voxel i, wherein $$D_i = \sum_{j=1}^{N} w_j D_{i,j}$$

with $D_{i,j}$ denoting a dose contribution of beam spot j at voxel i for unit fluence, N beam spots contributing to the dose $D_i$ at voxel i, and $w_j$ denoting a weighting factor of beam spot j and wherein the prescribed biological effect $\epsilon_T$ is given by $$\epsilon_T = \alpha_T^X D_T + \beta_T^X D_T^2$$

with $\alpha_T^X$ and $\beta_T^X$ being X-ray response parameters of the target and $D_T$ denoting a prescribed photon dose.

4. The inverse treatment planning method according to claim 1, wherein an objective function is minimized, which includes constraints relating to minimum and maximum biological effect levels for the target and maximum effect levels for organs at risk or normal tissue within the biological system.

5. The inverse treatment planning method according to claim 1, wherein the $\alpha_{i,j}$- and $\sqrt{\beta_{i,j}}$-components are derived from a radiobiological model or from measured data for $\alpha$ and $\beta$ as a function of depth in a single Bragg peak.

6. The inverse treatment planning method according to claim 1, wherein a constant value $\beta_{i,j}=\beta_i$ is set, which depends only on a tissue type at voxel i.

7. The inverse treatment planning method according to claim 1, wherein the $\alpha_{i,j}$-components are assumed to be laterally constant and are extracted from a single curve as a function of residual range, independent of an initial beam energy.

8. Use of an inverse treatment planning method for intensity modulated particle therapy for the treatment of a target within a biological system using at least two fields, each field comprising a plurality of Bragg peaks, the at least two fields being planned to place a defined number of beam spots j from different directions with certain weights $w_j$ within the target, wherein the inverse treatment planning method optimizes the weights $w_j$ of the beam spots for the at least two fields simultaneously in order to produce a prescribed biological effect within the target by minimizing an objective function based on biological effects $\epsilon$, the biological effects $\epsilon$ being treated in a linear-quadratic model which describes the biological effects in the target by two parameters $\alpha$ and $\beta$, where $\epsilon=\alpha D+\beta D^2$, D denoting a dose, and wherein the two parameters $\alpha$ and $\beta$ for each voxel i of the target $\alpha_i$ and $\beta_i$ are calculated as dose-averaged mean values of $\alpha_{i,j}$- and $\sqrt{\beta_{i,j}}$-components, which relate to all beam spots j contributing to a total dose $D_i$ in the voxel i for planning the treatment of a tumor with an ion beam containing ions with an atomic number $\geq 2$.

9. A radiation treatment apparatus for delivering a radiation treatment to a target within a biological system comprising
a field unit for generating at least two fields, each field comprising a plurality of Bragg peaks, the at least two fields being provided to place a defined number of beam spots j from different directions with certain weights $w_j$ within the target and
a unit for inverse treatment planning being provided for optimizing the weights $w_j$ of the beam spots for the at least two fields simultaneously before the radiation treatment in order to produce a prescribed biological effect within the target by minimizing an objective function based on biological effects $\epsilon$, the biological effects $\epsilon$ being treated in a linear-quadratic model, which describes the biological effects in the target by two parameters $\alpha$ and $\beta$, where $\epsilon=\alpha D+\beta D^2$, D denoting a dose, and wherein the two parameters $\alpha$ and $\beta$ for each voxel i of the target $(\alpha_i, \beta_i)$ are calculated as dose-averaged mean values of $\alpha_{i,j}$- and $\sqrt{\beta_{i,j}}$-components, which relate to all beam spots j contributing to a total dose $D_i$ in the voxel i.

* * * * *

UNITED STATES PATENT AND TRADEMARK OFFICE
CERTIFICATE OF CORRECTION

PATENT NO.           : 8,183,541 B2
APPLICATION NO.      : 12/223712
DATED                : May 22, 2012
INVENTOR(S)          : Jan Wilkens et al.

It is certified that error appears in the above-identified patent and that said Letters Patent is hereby corrected as shown below:

ON THE TITLE PAGE:

At item (73), Assignee, change "Deutsches Krebsforschungszentrum Des Oeffentlichen Rechts, Heidelberg (DE)", to --Deutsches Krebsforschungszentrum Stiftung Des Oeffentlichen Rechts, Heidelberg (DE)--.

Signed and Sealed this
Eleventh Day of September, 2012

David J. Kappos
*Director of the United States Patent and Trademark Office*